US009668739B2

(12) United States Patent
 Conklin et al.

(10) Patent No.: US 9,668,739 B2
(45) Date of Patent: Jun. 6, 2017

(54) SELF-CINCHING SURGICAL CLIPS AND DELIVERY SYSTEM

(71) Applicant: Edwards Lifesciences Corporation, Irvine, CA (US)

(72) Inventors: Brian S. Conklin, Orange, CA (US); James A. Davidson, San Juan Capistrano, CA (US); Ralph Schneider, Trabuco Canyon, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 83 days.

(21) Appl. No.: 14/637,177

(22) Filed: Mar. 3, 2015

(65) Prior Publication Data

US 2015/0173759 A1 Jun. 25, 2015

Related U.S. Application Data

(62) Division of application No. 13/693,952, filed on Dec. 4, 2012, now Pat. No. 8,968,336.

(60) Provisional application No. 61/568,048, filed on Dec. 7, 2011.

(51) Int. Cl.
 *A61B 17/10* (2006.01)
 *A61B 17/068* (2006.01)
 *A61B 17/064* (2006.01)

(52) U.S. Cl.
 CPC ............ *A61B 17/10* (2013.01); *A61B 17/064* (2013.01); *A61B 17/068* (2013.01); *A61B 17/105* (2013.01); *A61B 2017/0645* (2013.01); *A61B 2017/0649* (2013.01)

(58) Field of Classification Search
 CPC ..... A61B 17/10; A61B 17/064; A61B 17/068; A61B 17/105; A61B 17/122; A61B 17/1222; A61B 17/1227; A61B 17/128; A61B 17/1285; A61B 2017/0645; A61B 2017/0649; A61B 2017/1225; A61B 2576/023; A61F 2/2442; A61F 2/2427
 See application file for complete search history.

(56) References Cited

U.S. PATENT DOCUMENTS

| | | | |
|---|---|---|---|
| 2,264,679 A | 12/1941 | Ravel | |
| 2,516,710 A | 7/1950 | Mascolo | |
| 2,715,486 A | 8/1955 | Marcoff-Moghadam et al. | |
| 2,890,519 A | 6/1959 | Storz, Jr. | |
| 3,143,742 A | 8/1964 | Cromie | |
| 3,249,104 A | 5/1966 | Hohnstein | |
| 3,274,658 A | 9/1966 | Pile | |

(Continued)

*Primary Examiner* — Jocelin Tanner
(74) *Attorney, Agent, or Firm* — Guy Cumberbatch; Thomas C. Richardson

(57) ABSTRACT

A device and method for deploying self-cinching surgical clips. The device accesses at least two layers of tissue or material from only one side of the tissue or material and punctures through the two layers of tissue or material. The various configurations of clips disclosed herein are made of a superelastic material such as Nitinol, and have a constrained and a relaxed state, and no sharp edges or tips so as to reduce tissue irritation following deployment. The clip is disposed within the housing of the delivery device and held in a constrained state by a tube assembly until deployment wherein the clip assumes its relaxed state, where the ends of the clip are brought into close approximation, thereby securing the layers of tissue or material together.

15 Claims, 11 Drawing Sheets

(56) References Cited

U.S. PATENT DOCUMENTS

| | | |
|---|---|---|
| 3,452,742 A | 7/1969 | Muller |
| 3,506,012 A | 4/1970 | Brown |
| 3,509,882 A | 5/1970 | Blake |
| 3,541,591 A | 11/1970 | Hoegerman |
| 3,547,103 A | 12/1970 | Cook |
| 3,570,497 A | 3/1971 | Lemole |
| 3,608,095 A | 9/1971 | Barry |
| 3,638,654 A | 2/1972 | Akuba |
| RE27,391 E | 6/1972 | Merser |
| 3,753,438 A | 8/1973 | Wood et al. |
| 3,859,668 A | 1/1975 | Anderson |
| 3,875,648 A | 4/1975 | Bone |
| 3,898,999 A | 8/1975 | Haller |
| 3,910,281 A | 10/1975 | Kletschka et al. |
| 3,958,576 A | 5/1976 | Komiya |
| 3,976,079 A | 8/1976 | Samuels et al. |
| 3,988,810 A | 11/1976 | Emery |
| 3,996,623 A | 12/1976 | Kaster |
| 4,038,725 A | 8/1977 | Keefe |
| 4,103,690 A | 8/1978 | Harris |
| 4,140,125 A | 2/1979 | Smith |
| 4,170,990 A | 10/1979 | Baumgart et al. |
| 4,192,315 A | 3/1980 | Hilzinger et al. |
| 4,217,902 A | 8/1980 | March |
| 4,324,248 A | 4/1982 | Perlin |
| 4,345,601 A | 8/1982 | Fukuda |
| 4,416,266 A | 11/1983 | Baucom |
| 4,456,017 A | 6/1984 | Miles |
| 4,485,816 A | 12/1984 | Krumme |
| 4,522,207 A | 6/1985 | Klieman et al. |
| 4,535,764 A | 8/1985 | Ebert |
| 4,548,202 A | 10/1985 | Duncan |
| 4,549,545 A | 10/1985 | Levy |
| 4,586,502 A | 5/1986 | Bedi et al. |
| 4,586,503 A | 5/1986 | Kirsch et al. |
| 4,595,007 A | 6/1986 | Mericle |
| 4,612,932 A | 9/1986 | Caspar et al. |
| 4,637,380 A | 1/1987 | Orejola |
| 4,665,906 A | 5/1987 | Jervis |
| 4,683,895 A | 8/1987 | Pohndorf |
| 4,705,040 A | 11/1987 | Mueller et al. |
| 4,719,924 A | 1/1988 | Crittenden et al. |
| 4,730,615 A | 3/1988 | Sutherland et al. |
| 4,741,330 A | 5/1988 | Hayhurst |
| 4,743,253 A | 5/1988 | Magladry |
| 4,750,492 A | 6/1988 | Jacobs |
| 4,809,695 A | 3/1989 | Gwathmey et al. |
| 4,823,794 A | 4/1989 | Pierce |
| 4,863,460 A | 9/1989 | Magladry |
| 4,873,975 A | 10/1989 | Walsh et al. |
| 4,896,668 A | 1/1990 | Popoff et al. |
| 4,899,744 A | 2/1990 | Fujitsuka et al. |
| 4,901,721 A | 2/1990 | Hakki |
| 4,924,866 A | 5/1990 | Yoon |
| 4,926,860 A | 5/1990 | Stice et al. |
| 4,929,240 A | 5/1990 | Kirsch et al. |
| 4,932,955 A | 6/1990 | Merz et al. |
| 4,950,283 A | 8/1990 | Dzubow et al. |
| 4,950,285 A | 8/1990 | Wilk |
| 4,955,913 A | 9/1990 | Robinson |
| 4,976,715 A | 12/1990 | Bays et al. |
| 4,983,176 A | 1/1991 | Cushman et al. |
| 4,990,152 A | 2/1991 | Yoon |
| 4,997,439 A | 3/1991 | Chen |
| 5,002,550 A | 3/1991 | Li |
| 5,002,562 A | 3/1991 | Oberlander |
| 5,002,563 A | 3/1991 | Pyka et al. |
| 5,026,379 A | 6/1991 | Yoon |
| 5,047,047 A | 9/1991 | Yoon |
| 5,053,047 A | 10/1991 | Yoon |
| 5,070,805 A | 12/1991 | Plante |
| 5,071,431 A | 12/1991 | Sauter et al. |
| 5,074,874 A | 12/1991 | Yoon et al. |
| 5,078,731 A | 1/1992 | Hayhurst |
| 5,100,418 A | 3/1992 | Yoon et al. |
| 5,116,840 A | 5/1992 | Ganguly et al. |
| 5,123,913 A | 6/1992 | Wilk et al. |
| RE34,021 E | 8/1992 | Mueller et al. |
| 5,152,769 A | 10/1992 | Baber |
| 5,154,189 A | 10/1992 | Oberlander |
| 5,158,566 A | 10/1992 | Pianetti |
| 5,163,954 A | 11/1992 | Curcio et al. |
| 5,171,250 A | 12/1992 | Yoon |
| 5,171,251 A | 12/1992 | Bregen et al. |
| 5,171,252 A | 12/1992 | Friedland |
| 5,174,087 A | 12/1992 | Bruno |
| 5,196,022 A | 3/1993 | Bilweis |
| 5,219,358 A | 6/1993 | Bendel et al. |
| 5,222,976 A | 6/1993 | Yoon |
| 5,234,449 A | 8/1993 | Bruker et al. |
| 5,236,440 A | 8/1993 | Hlavacek |
| 5,242,456 A | 9/1993 | Nash et al. |
| 5,246,443 A | 9/1993 | Mai |
| 5,258,011 A | 11/1993 | Drews |
| 5,258,015 A | 11/1993 | Li et al. |
| 5,269,783 A | 12/1993 | Sander |
| 5,269,809 A | 12/1993 | Hayhurst et al. |
| 5,282,832 A | 2/1994 | Toso et al. |
| 5,290,289 A | 3/1994 | Sanders et al. |
| 5,304,204 A | 4/1994 | Bregen |
| 5,306,290 A | 4/1994 | Martins et al. |
| 5,306,296 A | 4/1994 | Wright et al. |
| 5,312,436 A | 5/1994 | Coffey et al. |
| 5,330,503 A | 7/1994 | Yoon |
| 5,336,239 A | 8/1994 | Gimpelson |
| 5,356,424 A | 10/1994 | Buzerak et al. |
| 5,374,268 A | 12/1994 | Sander |
| 5,383,904 A | 1/1995 | Totakura et al. |
| 5,383,905 A | 1/1995 | Golds et al. |
| 5,391,173 A | 2/1995 | Wilk |
| 5,403,346 A | 4/1995 | Loeser |
| 5,409,499 A | 4/1995 | Yi |
| 5,437,680 A | 8/1995 | Yoon |
| 5,437,685 A | 8/1995 | Blasnik |
| 5,439,479 A | 8/1995 | Shichman et al. |
| 5,445,167 A | 8/1995 | Yoon et al. |
| 5,450,860 A | 9/1995 | O'Connor |
| 5,452,733 A | 9/1995 | Sterman et al. |
| 5,456,246 A | 10/1995 | Schmieding et al. |
| 5,462,561 A | 10/1995 | Voda |
| 5,474,557 A | 12/1995 | Mai |
| 5,474,572 A | 12/1995 | Hayhurst |
| 5,480,405 A | 1/1996 | Yoon |
| 5,486,197 A | 1/1996 | Le et al. |
| 5,496,336 A | 3/1996 | Cosgrove et al. |
| 5,499,990 A | 3/1996 | Schulken et al. |
| 5,500,000 A | 3/1996 | Feagin et al. |
| 5,520,691 A | 5/1996 | Branch |
| 5,520,702 A | 5/1996 | Sauer et al. |
| 5,527,342 A | 6/1996 | Pietrzak et al. |
| 5,531,763 A | 7/1996 | Mastri et al. |
| 5,545,178 A | 8/1996 | Kensey et al. |
| 5,549,619 A | 8/1996 | Peters et al. |
| 5,569,274 A | 10/1996 | Rapacki et al. |
| 5,569,301 A | 10/1996 | Granger et al. |
| 5,582,616 A | 12/1996 | Bolduc et al. |
| 5,582,619 A | 12/1996 | Ken |
| 5,586,983 A | 12/1996 | Sanders et al. |
| 5,591,179 A | 1/1997 | Edelstein |
| 5,593,414 A | 1/1997 | Shipp et al. |
| 5,593,424 A | 1/1997 | Northrup, III |
| 5,609,608 A | 3/1997 | Benett et al. |
| 5,626,590 A | 5/1997 | Wilk |
| 5,630,824 A | 5/1997 | Hart |
| 5,632,752 A | 5/1997 | Buelna |
| 5,632,753 A | 5/1997 | Loeser |
| 5,643,289 A | 7/1997 | Sauer et al. |
| 5,643,295 A | 7/1997 | Yoon |
| 5,645,553 A | 7/1997 | Kolesa et al. |
| 5,645,568 A | 7/1997 | Chervitz et al. |
| 5,665,109 A | 9/1997 | Yoon |
| 5,669,917 A | 9/1997 | Sauer et al. |
| 5,669,935 A | 9/1997 | Rosenman et al. |
| 5,681,351 A | 10/1997 | Jamiolkowski et al. |

(56) References Cited

U.S. PATENT DOCUMENTS

| | | |
|---|---|---|
| 5,683,417 A | 11/1997 | Cooper |
| 5,695,505 A | 12/1997 | Yoon |
| 5,697,943 A | 12/1997 | Sauer et al. |
| 5,700,270 A | 12/1997 | Peyser et al. |
| 5,700,271 A | 12/1997 | Whitfield et al. |
| 5,707,380 A | 1/1998 | Hinchliffe et al. |
| 5,709,693 A | 1/1998 | Taylor |
| 5,709,695 A | 1/1998 | Northrup, III |
| 5,725,539 A | 3/1998 | Matern |
| 5,725,542 A | 3/1998 | Yoon |
| 5,725,556 A | 3/1998 | Moser et al. |
| 5,728,135 A | 3/1998 | Bregen et al. |
| 5,735,290 A | 4/1998 | Sterman et al. |
| 5,735,877 A | 4/1998 | Pagedas |
| 5,776,188 A | 7/1998 | Shepherd et al. |
| 5,799,661 A | 9/1998 | Boyd et al. |
| 5,810,851 A | 9/1998 | Yoon |
| 5,810,882 A | 9/1998 | Bolduc et al. |
| 5,820,631 A | 10/1998 | Nobles |
| 5,824,008 A | 10/1998 | Bolduc et al. |
| 5,830,221 A | 11/1998 | Stein et al. |
| 5,845,645 A | 12/1998 | Bonutti |
| 5,849,019 A | 12/1998 | Yoon |
| 5,861,004 A | 1/1999 | Kensey et al. |
| 5,879,371 A | 3/1999 | Gardiner et al. |
| 5,891,130 A | 4/1999 | Palermo et al. |
| 5,891,160 A | 4/1999 | Williamson, IV et al. |
| 5,895,393 A | 4/1999 | Pagedas |
| 5,895,394 A | 4/1999 | Kienzle et al. |
| 5,919,207 A | 7/1999 | Taheri |
| 5,948,001 A | 9/1999 | Larsen |
| 5,961,481 A | 10/1999 | Sterman et al. |
| 5,961,539 A | 10/1999 | Northrup, III et al. |
| 5,964,772 A | 10/1999 | Bolduc et al. |
| 5,972,024 A | 10/1999 | Northrup, III et al. |
| 5,976,159 A | 11/1999 | Bolduc et al. |
| 5,984,917 A | 11/1999 | Fleischman et al. |
| 5,989,242 A | 11/1999 | Saadat et al. |
| 5,989,268 A | 11/1999 | Pugsley, Jr. et al. |
| 5,997,556 A | 12/1999 | Tanner |
| 6,001,110 A | 12/1999 | Adams |
| 6,013,084 A | 1/2000 | Ken et al. |
| 6,015,428 A | 1/2000 | Pagedas |
| 6,039,176 A | 3/2000 | Wright |
| 6,066,160 A | 5/2000 | Colvin et al. |
| 6,074,409 A | 6/2000 | Goldfarb |
| 6,120,524 A | 9/2000 | Taheri |
| 6,132,438 A | 10/2000 | Fleischman et al. |
| 6,139,540 A | 10/2000 | Rost et al. |
| 6,143,004 A | 11/2000 | Davis et al. |
| 6,176,413 B1 | 1/2001 | Heck et al. |
| 6,190,373 B1 | 2/2001 | Palermo et al. |
| 6,193,733 B1 | 2/2001 | Adams |
| 6,193,734 B1 | 2/2001 | Bolduc et al. |
| 6,231,592 B1 | 5/2001 | Bonutti et al. |
| 6,241,765 B1 | 6/2001 | Griffin et al. |
| 6,254,615 B1 | 7/2001 | Bolduc et al. |
| 6,306,141 B1 | 10/2001 | Jervis |
| 6,346,112 B2 | 2/2002 | Adams |
| 6,368,334 B1 | 4/2002 | Sauer |
| 6,432,123 B2 | 8/2002 | Schwartz et al. |
| 6,475,230 B1 | 11/2002 | Bonutti et al. |
| 6,514,265 B2 | 2/2003 | Ho et al. |
| 6,537,290 B2 | 3/2003 | Adams et al. |
| 6,551,332 B1 | 4/2003 | Nguyen et al. |
| 6,589,279 B1 | 7/2003 | Anderson et al. |
| 6,607,541 B1 | 8/2003 | Gardiner et al. |
| 6,613,059 B2 | 9/2003 | Schaller et al. |
| 6,626,930 B1 | 9/2003 | Allen et al. |
| 6,641,592 B1 | 11/2003 | Sauer et al. |
| 6,641,593 B1 | 11/2003 | Schaller et al. |
| 6,682,540 B1 | 1/2004 | Sancoff et al. |
| 6,719,767 B1 | 4/2004 | Kimblad |
| 6,746,457 B2 | 6/2004 | Dana et al. |
| 6,749,622 B2 | 6/2004 | McGuckin, Jr. et al. |
| 6,776,784 B2 | 8/2004 | Ginn |
| 6,837,893 B2 | 1/2005 | Miller |
| 6,860,890 B2 | 3/2005 | Bachman et al. |
| 6,896,686 B2 | 5/2005 | Weber |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1* | 8/2005 | Nguyen ............ A61B 17/0469 606/151 |
| 6,945,980 B2 | 9/2005 | Nguyen et al. |
| 6,960,221 B2 | 11/2005 | Ho et al. |
| 7,011,669 B2 | 3/2006 | Kimblad |
| 7,083,628 B2 | 8/2006 | Bachman |
| 7,094,244 B2 | 8/2006 | Schreck |
| 7,112,207 B2 | 9/2006 | Allen et al. |
| 7,220,266 B2 | 5/2007 | Gambale |
| 7,235,086 B2 | 6/2007 | Sauer et al. |
| 7,264,625 B1 | 9/2007 | Buncke |
| 7,381,210 B2 | 6/2008 | Zarbatany et al. |
| 7,556,647 B2 | 7/2009 | Drews et al. |
| 7,628,797 B2 | 12/2009 | Tieu et al. |
| 7,678,077 B2* | 3/2010 | Harris ............... A61M 25/0068 604/108 |
| 7,731,727 B2 | 6/2010 | Sauer |
| 7,833,237 B2 | 11/2010 | Sauer |
| 7,842,051 B2 | 11/2010 | Dana et al. |
| 7,862,584 B2 | 1/2011 | Lyons et al. |
| 7,875,056 B2 | 1/2011 | Jervis et al. |
| 7,959,674 B2 | 6/2011 | Shu et al. |
| 8,021,421 B2 | 9/2011 | Fogarty et al. |
| 8,100,923 B2 | 1/2012 | Paraschac et al. |
| 8,105,355 B2 | 1/2012 | Page et al. |
| 8,252,005 B2 | 8/2012 | Findlay, III et al. |
| 8,398,657 B2 | 3/2013 | Sauer |
| 8,398,680 B2 | 3/2013 | Sauer et al. |
| 8,603,161 B2 | 12/2013 | Drews et al. |
| 2003/0055409 A1 | 3/2003 | Brock |
| 2003/0105473 A1* | 6/2003 | Miller .................. A61B 17/064 606/139 |
| 2003/0109922 A1 | 6/2003 | Peterson et al. |
| 2005/0131429 A1* | 6/2005 | Ho .................... A61B 17/06109 606/143 |
| 2005/0267495 A1* | 12/2005 | Ginn .................. A61B 17/0057 606/151 |
| 2006/0135967 A1* | 6/2006 | Realyvasquez ...... A61B 17/072 606/142 |
| 2007/0088391 A1 | 4/2007 | McAlexander et al. |
| 2007/0270907 A1 | 11/2007 | Stokes et al. |
| 2008/0255591 A1 | 10/2008 | Harada et al. |
| 2008/0281356 A1 | 11/2008 | Chau et al. |
| 2009/0143821 A1 | 6/2009 | Stupak |
| 2010/0324597 A1 | 12/2010 | Shikhman |
| 2011/0087242 A1 | 4/2011 | Pribanic et al. |
| 2011/0224714 A1 | 9/2011 | Gertner |
| 2011/0283514 A1 | 11/2011 | Fogarty et al. |
| 2013/0110164 A1 | 5/2013 | Milazzo et al. |
| 2014/0100652 A1 | 4/2014 | Drews et al. |

* cited by examiner

Fig. 4
Fig. 5
Fig. 6
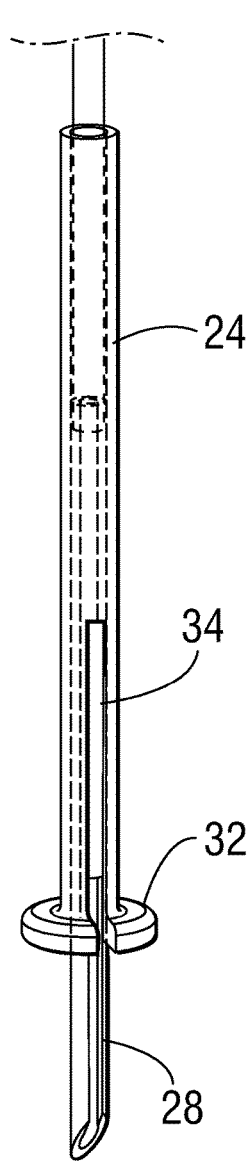
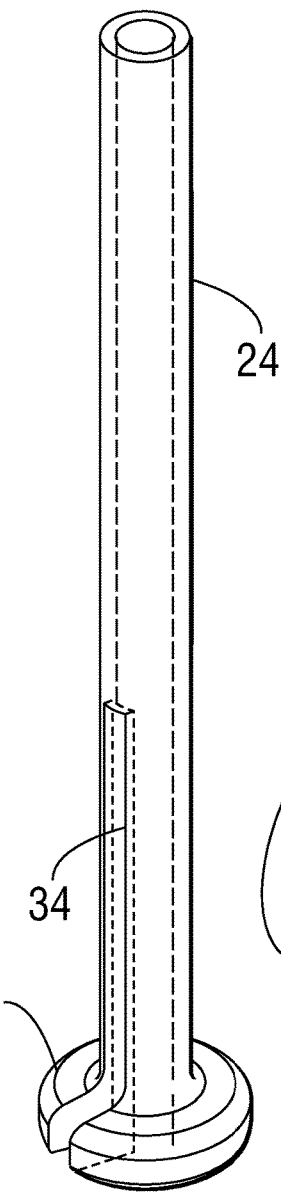
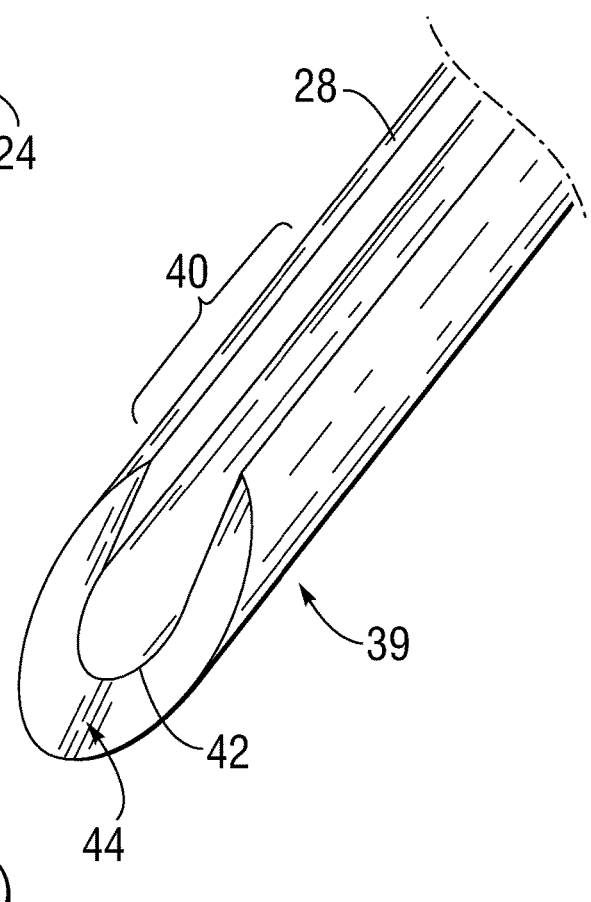

Fig. 7A
Fig. 7B
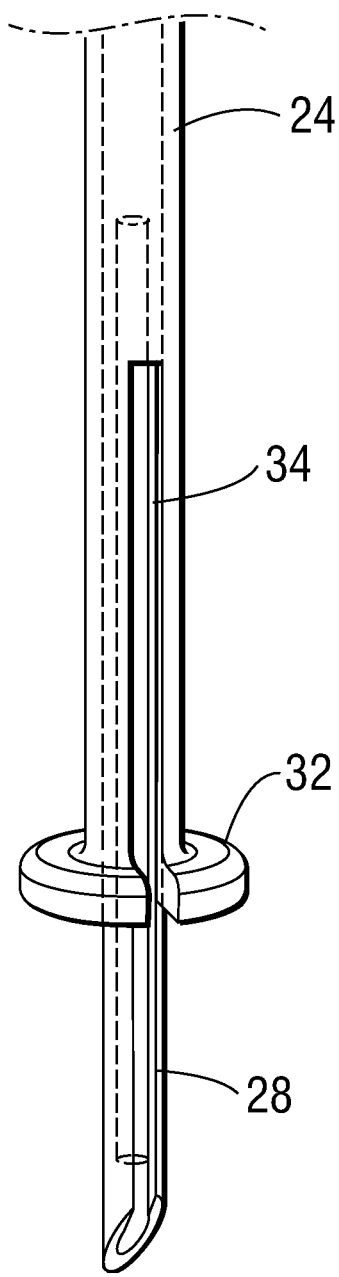
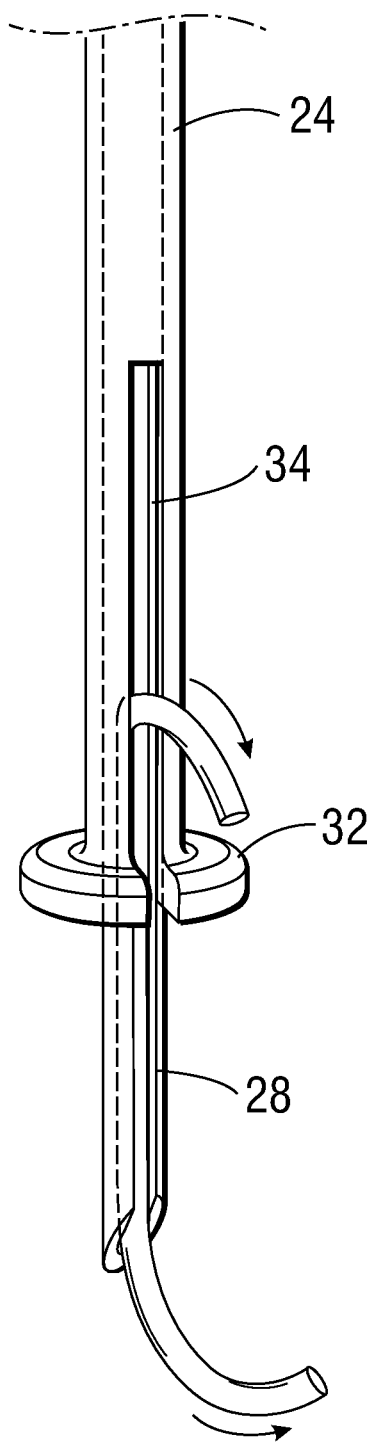

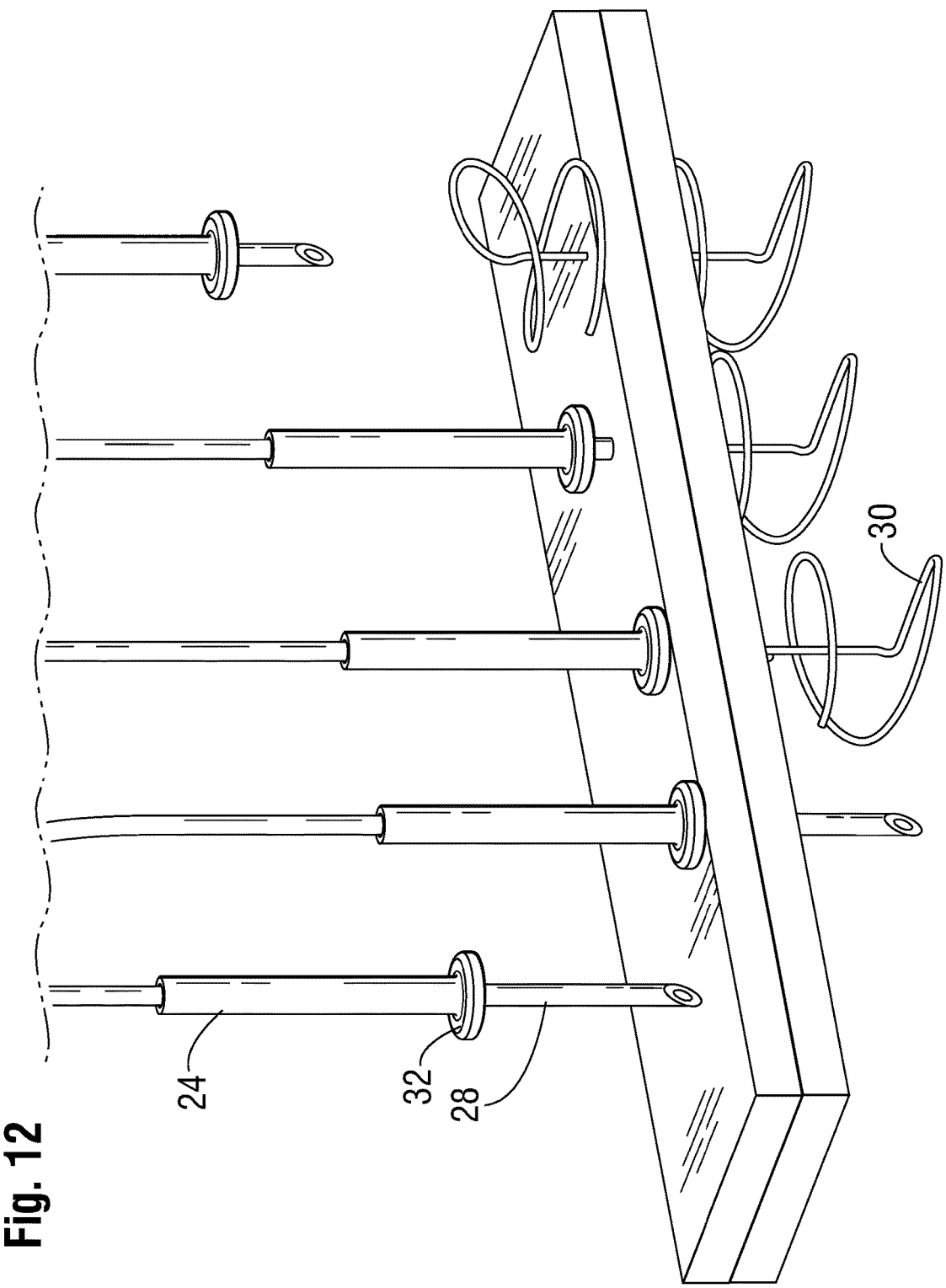

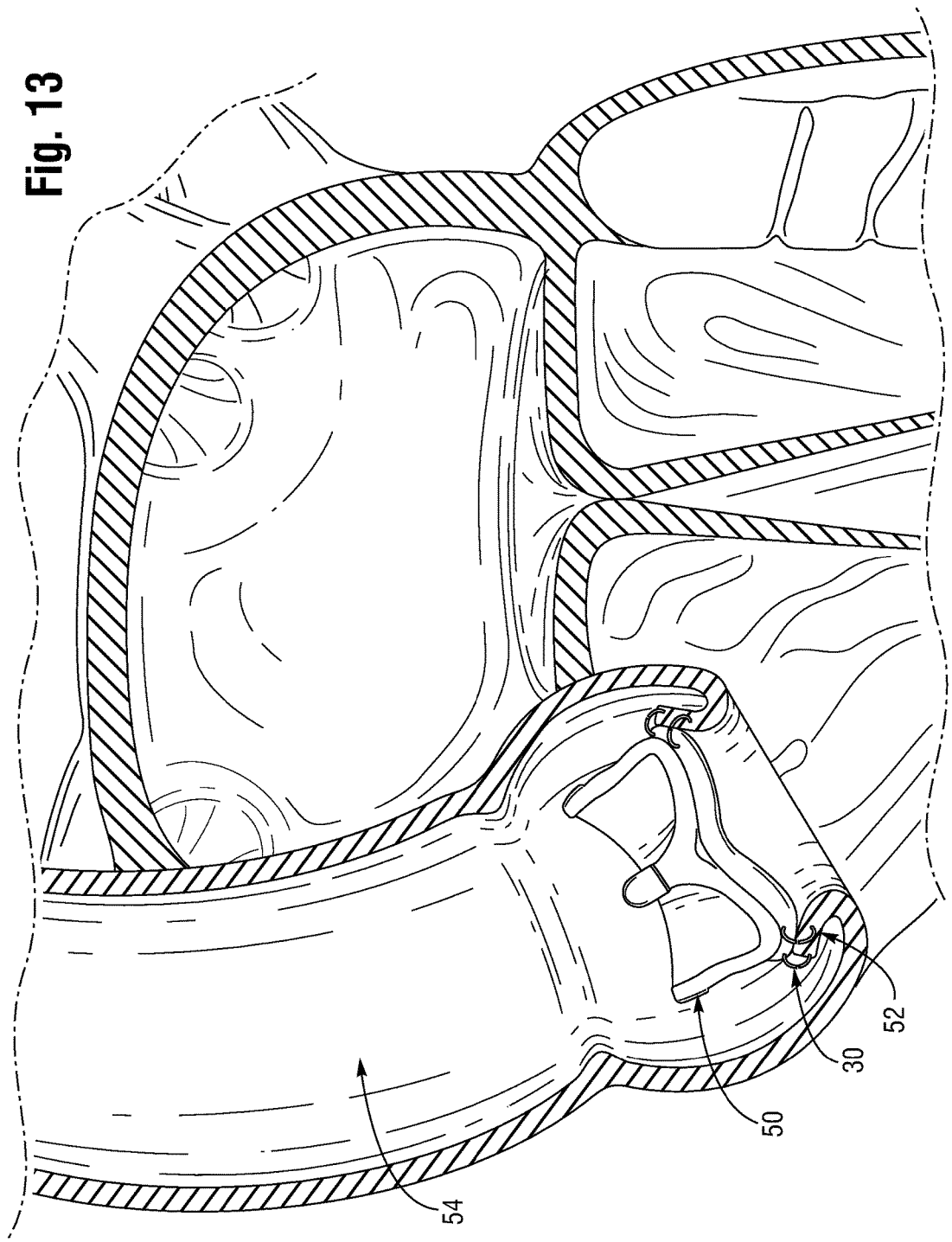

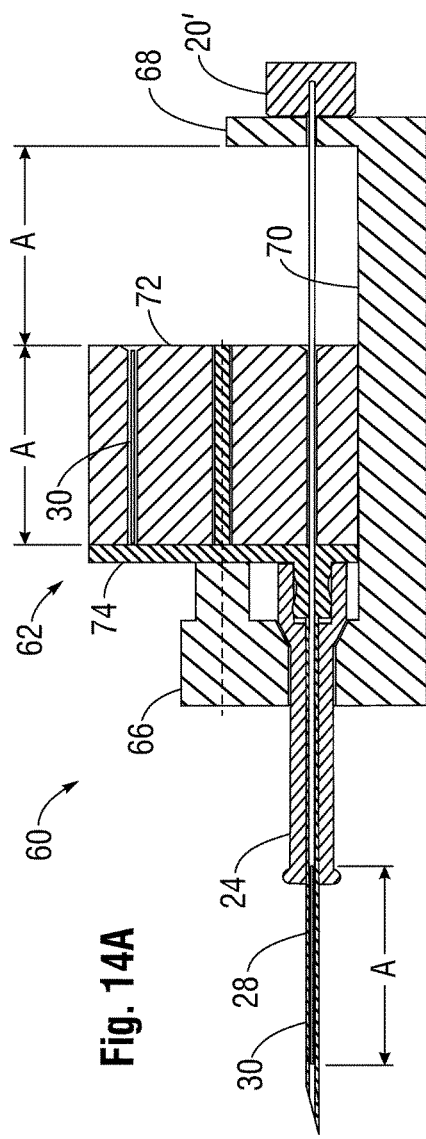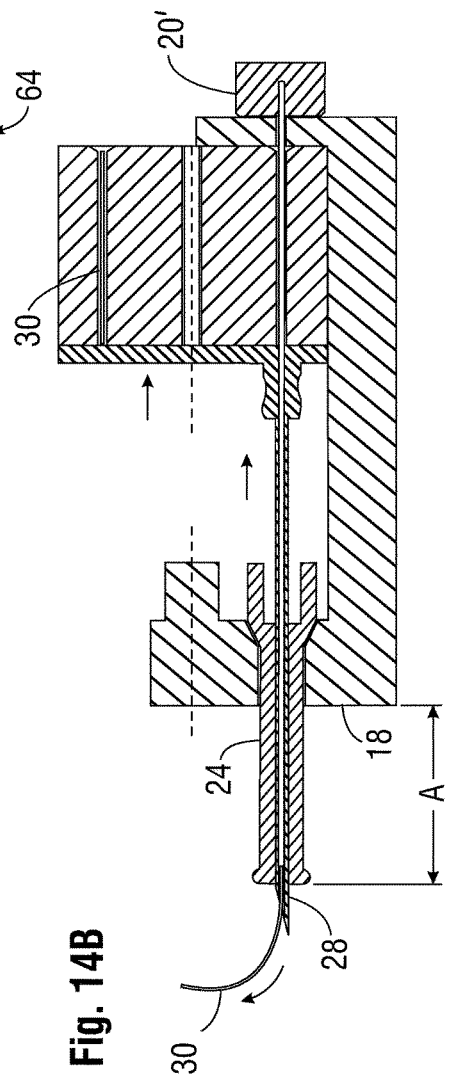
Fig. 14A
Fig. 14B

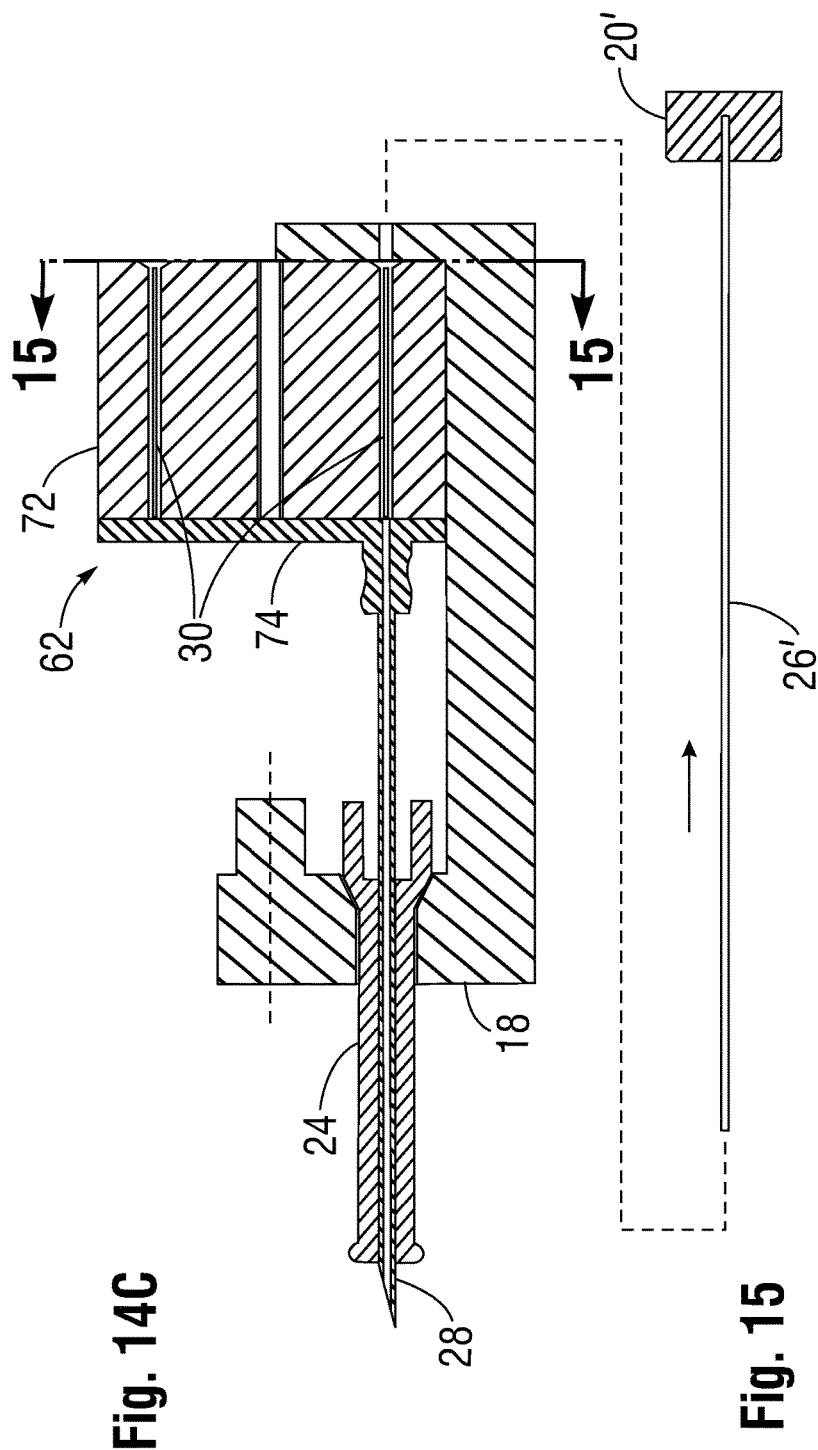

SELF-CINCHING SURGICAL CLIPS AND DELIVERY SYSTEM

RELATED APPLICATIONS

This application is a divisional of U.S. patent application Ser. No. 13/693,952, filed Dec. 4, 2012, now U.S. Pat. No. 8,968,336, which claims the benefit of U.S. Patent Application No. 61/568,048, filed Dec. 7, 2011, the disclosures all of which are incorporated by reference in their entireties.

FIELD OF THE INVENTION

The present invention relates generally to the field of medical devices. More particularly, this application relates to self-cinching clips and clip delivery systems for use in surgical procedures.

BACKGROUND OF THE INVENTION

Prosthetic heart valves are used to replace damaged or diseased heart valves. The natural heart valves are the aortic, mitral (or bicuspid), tricuspid and pulmonary valves. Prosthetic heart valves can be used to replace any of these naturally occurring valves. Repair or replacement of the aortic or mitral valves is most common because they reside in the left side of the heart where pressures are the greatest.

Where replacement of a heart valve is indicated, the dysfunctional valve is typically cut out and replaced with either a mechanical valve or a tissue valve. Typically, an artificial valve has flexible (e.g., bioprosthetic) leaflets attached to a wireform structure with arcuate cusps and upstanding commissures supporting the leaflets within the valve. The artificial valve also has an annular stent and a soft sewing ring for better attachment to and sealing against the native valve annulus. The alternating cusps and commissures mimic the natural contour of leaflet attachment. Importantly, the wireform provides continuous support for each leaflet along the cusp region so as to better simulate the natural support structure.

In a typical prosthetic heart valve implantation, approximately 12-18 sutures are placed through the patient's native valve annulus. These sutures are subsequently passed through the sewing ring of the prosthetic valve outside of the surgical cavity. The valve is then "parachuted" down these sutures to the point where it meets the target annulus. At that point, the sutures are tied to secure the prosthesis to the heart. The process of placing the sutures through the annulus and subsequently tying 3-10 knots per suture is very time consuming and greatly adds to the time the patient is on heart-lung bypass, anesthesia, etc. There is a direct correlation between time spent on heart-lung bypass and poor outcomes. Additionally, for mitral valves, there is the possibility of "suture looping" to occur during knot tying in which the suture is looped over a valve commissure and partially constrains a pair of valve leaflets, thus preventing normal function of the prosthesis.

Various methods of attaching a prosthetic heart valve to a heart with few or no sutures have been developed in the past. Attempted attachment methods include the utilization of hooks or barbs integrated into the prosthesis that bite into the native tissue to anchor the device. These devices have bulky delivery systems and it can be difficult to position the prosthesis accurately.

Another possible solution is to implant a valve in much the same way as traditionally done with sutures, but to replace most or all of the sutures with rapidly deploying clips to attach the sewing ring to the annulus. Past designs have disclosed instrumentation that would deploy a clip with sharpened edges necessary to puncture the tissues or materials that are to be secured together. Such designs with sharp-ended clips have created local tissue irritation due to the exposed ends.

Most of the current devices, such as those disclosed in U.S. Pat. Nos. 5,480,406; 6,913,607; 7,407,505; and 7,862,572 all require access to both sides of the tissue/structures which are being sewn/clipped together. This is of particular disadvantage in attaching a prosthetic heart valve to an annulus because the prosthetic valve impedes access to the inflow side of the annulus.

It would therefore be desirable to develop a method of attaching a prosthetic heart valve to a valve annulus with few or no sutures, using a smaller device to deliver the clips which requires access to only one side of the target. It would also be advantageous to have a deployment mechanism with a clip with no sharp edges or tips so as to reduce tissue irritation.

SUMMARY OF THE INVENTION

The present invention provides an instrument for use in intricate, minimally-invasive procedures. More specifically, the present disclosure discusses a device for securing a surgical clip to secure at least two layers of tissue and/or synthetic materials together, for example, to secure a sewing ring of a prosthetic heart valve to a native valve annulus.

In some embodiments the delivery device comprises a housing, a pusher assembly, and a substantially straight tube assembly. A self-cinching clip made of a super-elastic material is disposed within the tube assembly, said clip having a relaxed configuration and a constrained configuration. The tube assembly comprises an outer tube and inner tube slidably disposed within the outer tube, the inner tube having a sharpened end configured to puncture at least two layers of tissue or material. In some embodiments, the outer tube comprises a sharpened end configured to puncture the at least two layers of tissue or material. The outer tube can include a stop flange. The device can further include a revolving cylinder holding at least one clip, where each clip is in a separate chamber and each chamber is arranged around the perimeter of the revolving cylinder.

The self-cinching clip preferably is made of Nitinol (highly flexible Ni—Ti alloy). In its relaxed state the ends of the clip are brought into close approximation. For instance, the clip can have a spiral shape having two open ends terminating at different but closely-spaced locations, or a circular shape with two ends terminating at approximately the same location, or a semicircle shape with two ends of the clip overlapping.

The present invention also provides for a method for securing at least two layers of tissue or material together comprising the steps of: advancing a securing device toward at least two layers of tissue or material, the securing device containing a clip and a tube assembly, wherein the tube assembly has a sharpened end and wherein the clip is made of a super-elastic material and is constrained in a substantially straight position within the tube assembly; puncturing from only one side of the at least two layers of tissue or material through the at least two layers of tissue or material using the sharpened end of the tube assembly; and deploying said clip into the at least two layers of tissue or material, wherein the clip returns to its relaxed shape as it exits the tube assembly such that the ends of the clip are brought into close approximation, thereby securing the at least two layers together.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained and other advantages and features will appear with reference to the accompanying schematic drawings wherein:

FIG. 4 is a perspective view of a variation of the distal end of the clip delivery device of FIG. 1, showing an outer tube, an inner tube and clip release slots in each.

FIG. 5 is an enlarged view of the distal end of the outer tube of the clip delivery device.

FIG. 6 is an enlarged view of the distal end of the inner tube of the clip delivery device.

FIG. 7A is a perspective view of the distal end of the clip delivery device of FIGS. 4-6 showing an exemplary clip loaded into the inner tube of the clip delivery device prior to deployment.

FIG. 7B is a perspective view of the distal end of the clip delivery device of FIGS. 4-6 showing an exemplary clip exiting the inner tube of the clip delivery device during deployment.

FIG. 12 is a perspective view of the distal end of the clip delivery device of FIG. 1 illustrating the sequential steps of deploying a spiral clip into two layers of tissue and/or synthetic materials.

FIG. 13 is a perspective view of a prosthetic heart valve implant secured within a native heart valve annulus with the clips described herein.

FIGS. 14A-14C are cross-sectional views through an alternative clip delivery system having a cartridge that holds multiple clips, and FIG. 15 is an elevational view of the cartridge showing it rotating to present a new clip to be delivered.

DETAILED DESCRIPTION OF THE PREFERRED EMBODIMENTS

The following description refers to the accompanying drawings, which illustrate specific embodiments of the invention. Other embodiments having different structures and operation do not depart from the scope of the present invention.

Described herein is a surgical clip delivery device, which includes a self-closing surgical clip made of a superelastic or shape-memory material such as Nitinol, and methods for delivering the clip to a surgical site. While the device will be described in connection with a heart valve replacement procedure, it is to be understood that the device can be used in general surgery or in any procedure where two or more materials or layers are joined together. Its use is thus not limited to the surgical replacement of cardiac valves.

The self-closing surgical clip is designed such that when it is deformed into a configuration for delivery, the strains in the clip are below the yield point of the superelastic material. The clip is held within the delivery device in a constrained state and returns to its relaxed state once it is deployed from the delivery device. Specifically, when the clip is released from its constrained state, it returns or transitions toward its relaxed shape where the ends of the clip are brought into close approximation, thereby securing multiple layers of tissue or material together. It should be understood that intervening tissue or material may impede the clip from entirely resuming its relaxed shape, though the clips are designed to revert as near as possible to their relaxed states and thereby fasten the layers of tissue or material together.

Figure 1:
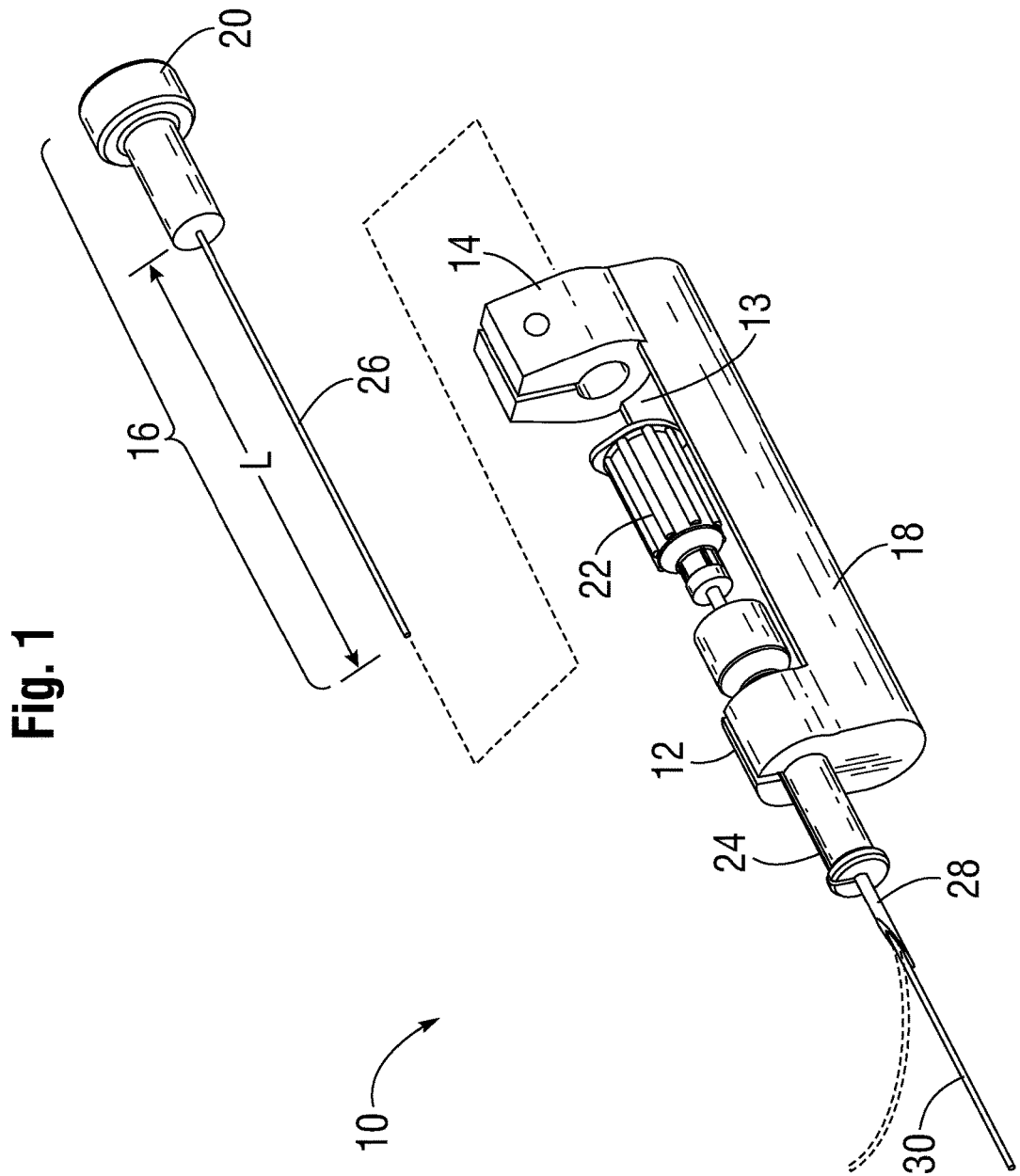
FIG. 1 is a perspective view of one embodiment of a surgical clip delivery system.
Figure 2:
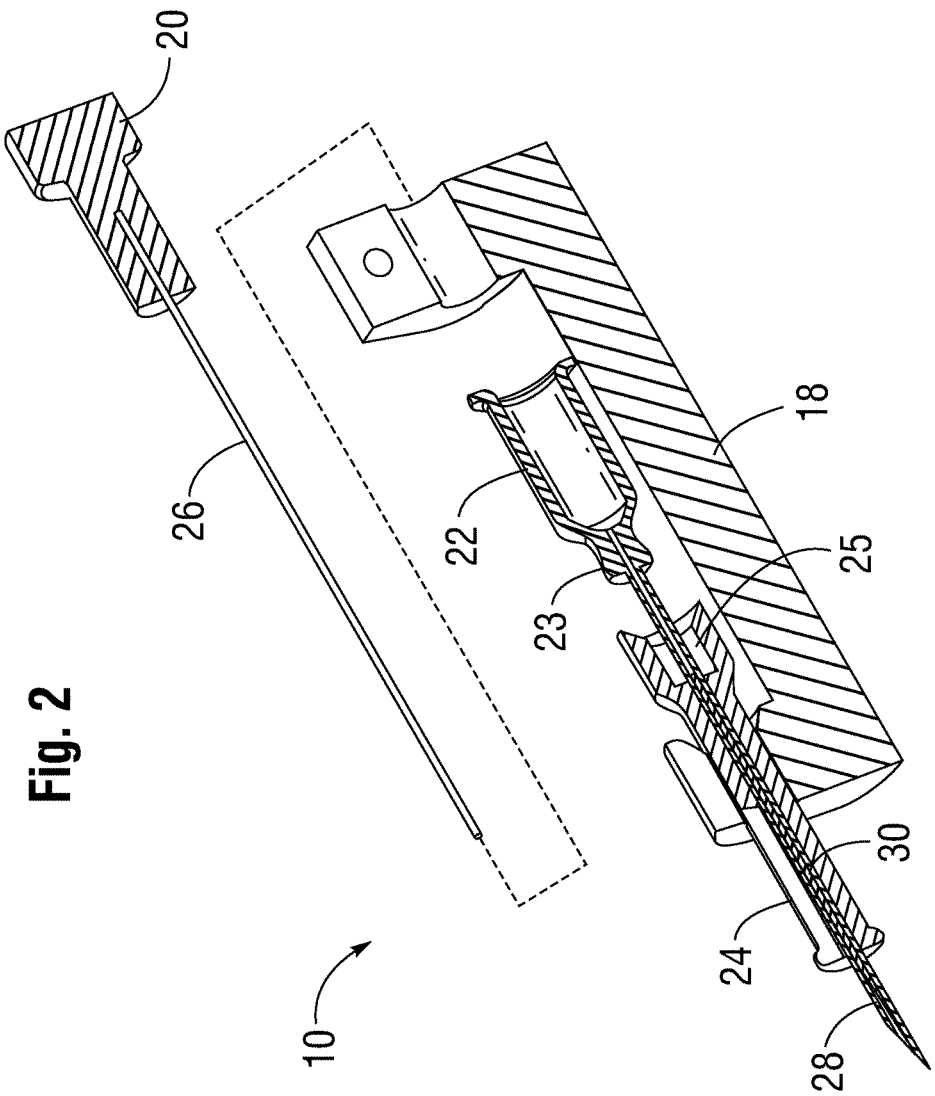
FIG. 2 is a cross-sectional view of the clip delivery system of FIG. 1.

FIGS. 1 and 2 illustrate an exemplary embodiment of a surgical clip delivery device 10. The device 10 comprises a housing 18 having a proximal end (to the right) and a distal end (to the left). A pusher assembly 16 includes a pusher handle 20 and a pusher shaft 26. The distal end of the device 10 contains a distal wall 12 through which an outer tube 24 and a hollow inner needle 28 extend distally from a graspable hub 22. The outer tube 24 is mounted for longitudinal movement through a bore in the distal wall 12 in the distal end of the housing 18, and the inner needle 28 slides within the lumen of the outer tube 24, as shown in cross-section in FIG. 2. Furthermore, the graspable hub 22 has a nipple 23 that removably couples with a short bore 25 in the proximal end of the outer tube 24 so that the two elements may be temporarily coupled together and slide together back and forth along a channel 13 of the housing between the distal wall 12 and a proximal wall 14.

Figure 3:
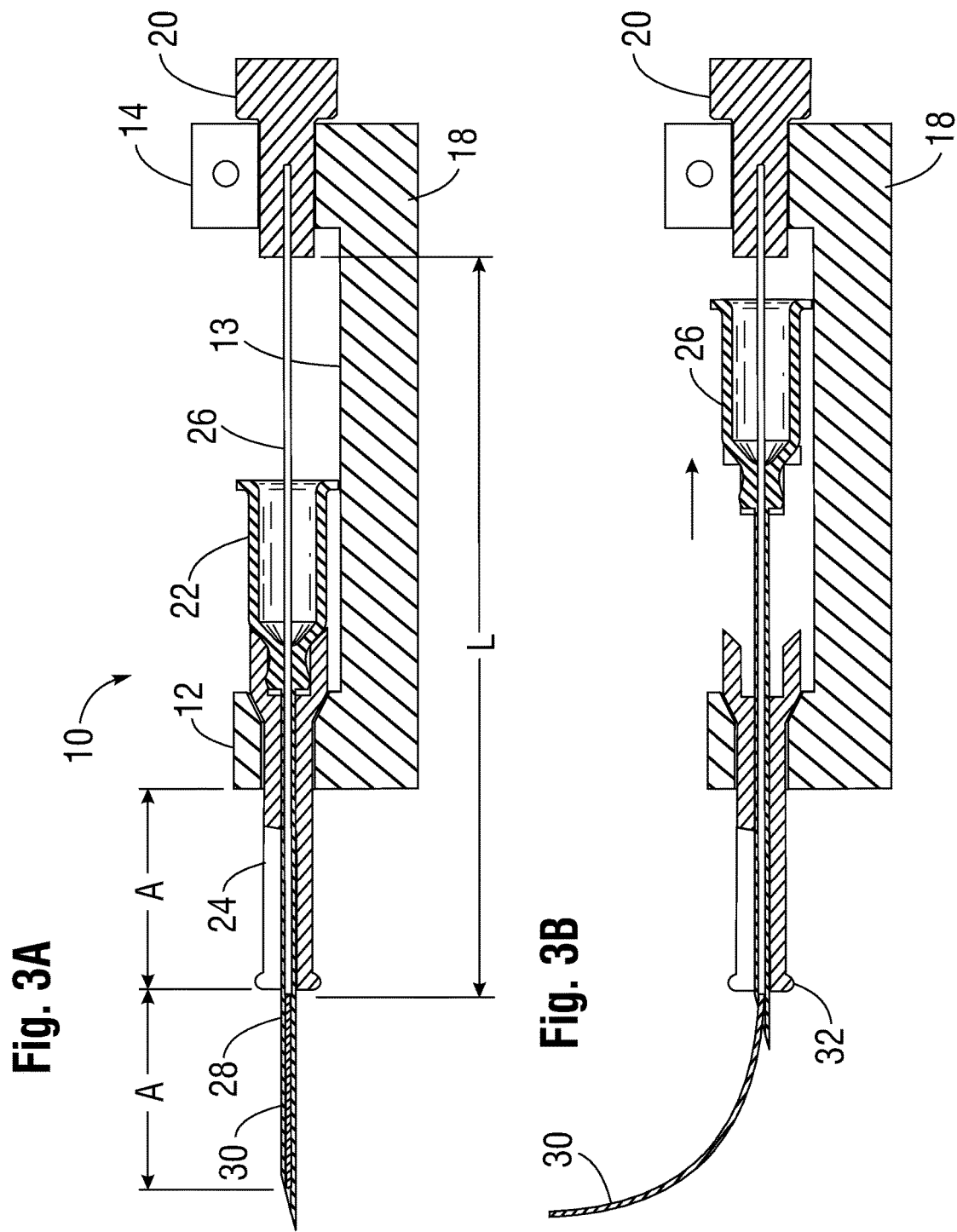
FIGS. 3A-3B are cross-sectional views of the clip delivery system in several stages of operation to eject a clip therefrom.

The pusher assembly 16 functions to deploy a self-cinching surgical clip 30 out of the inner needle 28 of the device and prevent the clip from backing out of the tissue or material. In this regard, a clip 30 is first loaded into the lumen of the inner needle 28 and the shaft 26 of the pusher assembly 16 advanced to locate the clip near the distal end of the needle 28, as seen in FIG. 3A. In this position, the coupled outer tube 24, inner needle 28 and graspable hub 22 are located to the left (or distally) within the channel 13. While the clip 30 is within the inner needle 28, it is constrained in a substantially straight position (or takes the shape of the inner needle 28 if that is not straight).

Both the inner needle 28 and outer tube 24 guide the clip 30 from the housing 18 into the tissue or material during deployment. FIG. 3B shows the delivery step where the user displaces the inner needle 28 and graspable hub 22 to the right a distance A along the channel 13, which is about the clip length, while the pusher assembly 16 remains in place relative to the housing 18. The pusher shaft 16 has a length L sufficient to urge the clip 30 from the end of the inner needle 28. The outer tube 24 also remains in place, preferably with a stop flange 32 staying in contact with the tissue or material layer, as will be explained.

FIGS. 4-5 present a detailed view of alternative embodiments of the outer tube 24 and the inner needle 28 of the delivery device 10. Outer tube 24 is an elongate tube having the stop flange 32 positioned at its distal end and, in the illustrated embodiment, axial slot 34 that extends from the stop flange a short distance proximally. The stop flange 32 prevents the outer tube 24 from penetrating the tissue or material too deeply. Slot 34 may be present to allow the clip 30 to assume a curved shape once the clip 30 has reached a certain point of deployment within the inner needle 28, as will be explained in more detail below.

As shown best in FIG. 4, in one particular embodiment the distal end of the inner needle 28 has a sharpened end 39 which assists in the insertion of the inner needle 28 into the tissue or material. The term, "sharpened end" will be used herein to represent sharpened tips, whether beveled, tapered, or some other configuration. The sharpened end 39 of the inner needle 28 of the delivery system 10 is used to puncture the tissue and/or prosthetic device. This obviates the need for the end of the clip 30, which remains inside of the inner needle 28 of the delivery device 10, to be sharp, and it is thus desirably blunt. Therefore, no sharp ends remain in the patient's body once the clips 30 are deployed. This is important in reducing irritation of the surrounding tissue and increases the safety of the clips 30 after implantation. It is well known that leaving clips or other devices in the body that have exposed sharp ends can cause irritation and necrosis of the surrounding tissue. Additionally, sharp tips have the potential to pierce other adjacent organs and therefore present a risk. In a preferred embodiment the free ends of each clip have been ground so as to be rounded and not even have right angle corners.

As shown in FIG. 6, the inner needle 28 of the delivery device 10 has a clip channel 42 to allow for passage and deployment of clip 30. In some embodiments, the clip channel 42 extends from a point between the proximal and distal ends of the inner needle 28 to the distal end of the inner needle 28. A single clip or multiple clips end-to-end in series can be pre-loaded within the inner needle 28 of the device prior to use. The combination of the outer tube 24 and inner needle 28 of FIGS. 4-6 permit the clip 30 to exit laterally from within the inner needle 28, through the aligned axial slot 34 and clip channel 42, as will be explained, in contrast to being ejected from a distal end as in FIGS. 1-3.

FIGS. 7A and 7B are additional detailed illustrations of the clip 30 as it is deployed from the outer tube 24 and inner needle 28 of FIGS. 4-6. In this embodiment, as the clip 30 exits the inner needle 28, it is no longer constrained in a straight position by the inner needle 28 and it therefore relaxes into its "no-stress" state shown in FIGS. 8-10, depending on the clip embodiment utilized. Due to its ability to return to its pre-shaped unconstrained closed-end shape, the clip 30 can be referred to as self-closing. The interaction of the outer tube 24 and inner needle 28 is such that relative rotation of one with respect to the other can alternately align and misalign the axial slot 34 and clip channel 42, so as to control the timing of the clip ejection. That is, first the clip 30 is urged to the end of the inner needle 28, and then the axial slot 34 and clip channel 42 are aligned to permit the clip 30 to curl and enter the target tissue or material layers.

Figure 10:
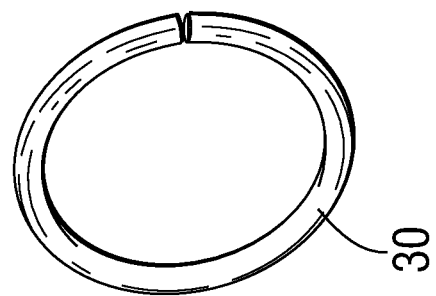
FIG. 10 is a perspective view of a circular-shaped clip embodiment of the present invention.
Figure 9:
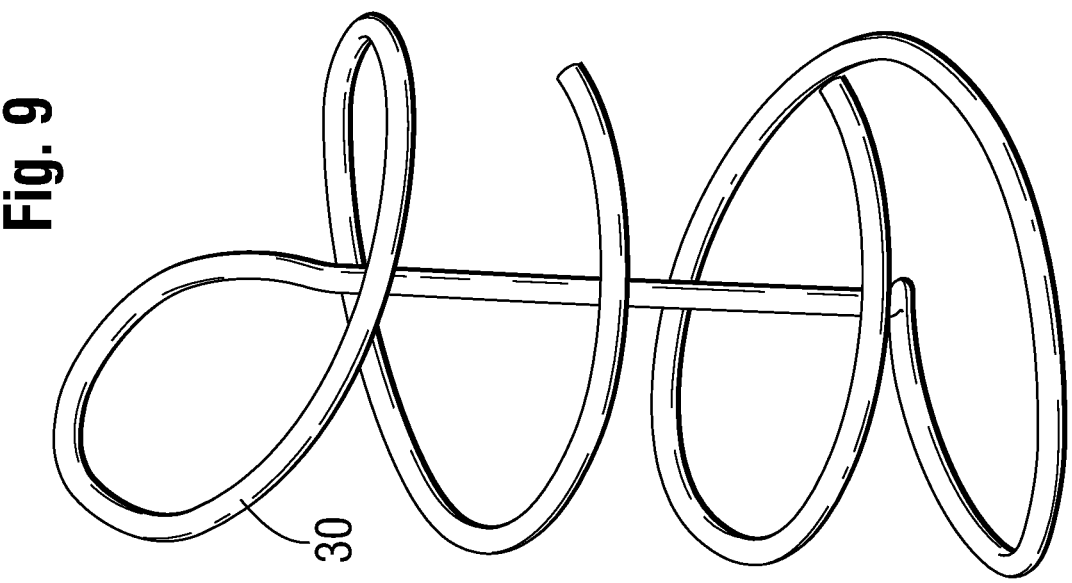
FIG. 9 is a perspective view of a spiral-shaped clip embodiment of the present invention.
Figure 8:
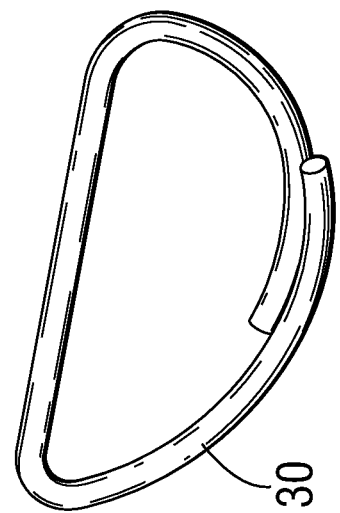
FIG. 8 is a perspective view of a semicircle-shaped clip embodiment of the present invention.

As shown in FIGS. 8-10, the clips can have a variety of shapes in their unstressed or unconstrained condition. Such shapes include semicircle-shaped (FIG. 8), modified spiral (FIG. 9), and circular (FIG. 10). The clip 30 is preferably made of a superelastic shape-memory material such as Nitinol so that when unconstrained, the clips 30 are self-closing toward their no-stress configurations. In each of the possible configurations, the clip 30 is designed such that when it is deformed into a delivery configuration the strains in the clip 30 are below the yield point of the superelastic material. In all configurations, the clip 30 does not have any sharp ends or edges.

In some of the variations presented here, such as the semicircle-shaped clip type shown in FIG. 8, the two ends of the clip overlap when deployed. This serves to reduce tissue irritation and increase the anchoring force to the tissue. In other embodiments, such as the circular clip shown in FIG. 10, the clip ends come together after deployment, thereby eliminating any exposed ends and reducing the potential for tissue irritation. The overlap of the two ends of the circular clip of FIG. 10 may further reduce tissue irritation as well as increase the holding force that can be generated by the clip. In other embodiments, such as the spiral configuration shown in FIG. 9, the clip has two open ends both terminating near the center of the clip.

The wire of the clips may have a round cross section, however, the cross section could be other shapes including, but not limited to, rectangular, triangular, etc. The cross section shape and dimension of the clip wire could also vary along its length to create variable amounts of stiffness in different portions of the clip. For example, with respect to the spiral clip 30 shown in FIG. 9, stiffness can be variable based upon the cross-sectional thickness, and the number and pitch of each individual coil. The overall shape of the clips could change as well and should not be considered limited to the three shapes disclosed herein.

Figure 11:
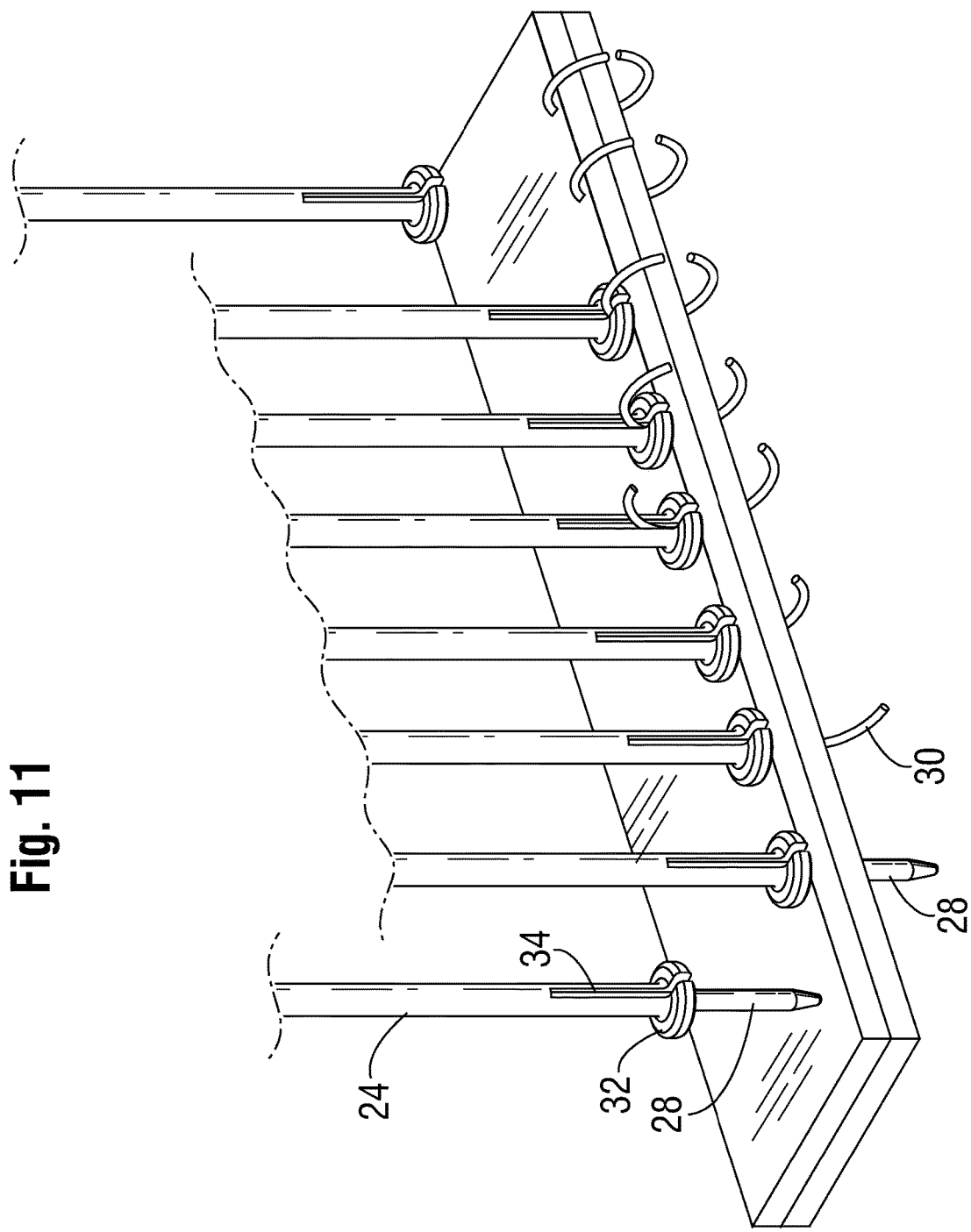
FIG. 11 is a perspective view of the distal end of the clip delivery device of FIGS. 4-6 illustrating the sequential steps of deploying a circular clip into two layers of tissue and/or synthetic materials.

The deployment sequence of a particular embodiment utilizing a circular clip 30 is shown in FIG. 11. First, the surgical clip delivery device 10 seen in FIG. 1 is advanced to the target site where the clip 30 is to be deployed. The surgeon pierces the sharp end of the inner needle 28 completely through the layers of tissue and/or synthetic materials to be fastened together. The stop flange 32 prevents the outer tube 24 from penetrating the tissue or material too deeply. Deployment of the clip 30 occurs as the pusher assembly 16 (not shown, see FIG. 1) is advanced distally toward the housing 18. In one particular embodiment, the distal end of the pusher shaft 26 is lined up end-to-end with the proximal end of the clip 30 within the inner needle 28 assembly. Distal advancement of the pusher shaft 26 therefore causing distal advancement of the clip 30. In another particular embodiment, the pusher assembly 16 remains static at the proximal end of the delivery device 10 as a stopper to prevent clip 30 from backing out of the proximal end of the inner needle 28.

In yet another embodiment, to deploy the clip 30, the pusher assembly 16 is advanced distally toward the housing 18 causing distal advancement of the clip 30 as described above. However, only a portion of the clip 30 is deployed this way, the remaining portion being deployed when the inner needle 28 is retracted proximally. The pusher assembly 16 moves distally a distance equal to only a portion of the length of the clip 30, exposing that portion of the clip 30 on the distal side of the tissue layers. The entire device 10 is then retracted exposing the proximal end of the clip 30 on the proximal side of the target. Alternatively, the clip 30 can be advanced using any other tool advancement mechanism known in the art.

Referring again to FIG. 11, the delivery sequence is as follows: the delivery device 10 is positioned over, and the distal end of the inner needle 28 pierces through, the target layers. The pusher assembly 16 that displaces the clip 30 is advanced forward until the clip 30 is completely deployed. The delivery device 10 is then removed. In some embodiments, the clip 30 is restrained within the inner needle 28 and the outer tube 24 until the tubes are rotated with respect to each other and their respective slots 34 and 40 are aligned allowing the clip 30 to be released from the tubes 28, 24.

Similarly, an example delivery sequence for the spiral clip 30 is shown in FIG. 12. In this particular embodiment, the device 10 is placed in a location proximate the target layers. The inner needle 28, having a sharpened and/or slanted end 39, pierces the target layers until the stop 32 hits the top layer. The clip 30 is deployed when the pusher assembly 16 (not shown) is advanced distally toward the housing 18. This action causes the clip 30 to begin exiting the distal end of the inner needle 28. As the clip 30 advances into the tissue, it begins to spiral around the axis of the inner needle 28 on the opposite side of the layers from the device 10. When the clip 30 is fully deployed, in one particular embodiment, portions of the clip 30 as well as the two ends of the clip are on opposite sides of the layers. In other embodiments, the ends may have varied final locations with respect to each other and varying portions of the clip may be on either side of the layers being held together by the clip 30. In some embodiments, once a sufficient portion of the clip 30 is deployed on the opposite side of the layers, the inner needle 28 is removed from the layer before the clip 30 is fully deployed to allow a portion of the clip 30 to be on the device-side of the layers.

FIG. 13 illustrates an artificial heart valve implanted within the aortic valve annulus utilizing the device 10 and clips 30 described herein. The prosthetic heart valve 50 is surgically inserted via the aorta 54 near the location of the native aortic heart valve annulus 52. The clip delivery device 10 is then inserted into the aorta 54 and the inner needle 28 first pierces the valve's securing ring and then the native valve annulus 52. The clip 30 is deployed as described above in connection with regarding FIGS. 11 and 12, securing the two layers (i.e., the valve's securing ring and the native valve annulus) together. Advantageously, the clips 30 shown in FIG. 13 were deployed entirely from the outflow side of the valve. The device disclosed herein is able to deliver the clips "blindly," i.e. with access to only one side of the target.

To facilitate installation of a number of the clips 30, the delivery device may include a cartridge of clips that periodically increments to present a new clip to be delivered. For example, FIGS. 14A-14C are cross-sectional views through an alternative clip delivery system 60 having a cartridge 62 that holds multiple clips 30. As in the single-clip version of the surgical clip delivery device 10, the system 60 has a housing 64 with a distal wall 66, a proximal wall 68, and a channel 70 therebetween and within which the cartridge 62 linearly reciprocates. FIG. 15 is an elevational view of the cartridge 62. A cylinder 72 portion of the cartridge 62 rotates about a shaft extending from a non-rotating portion 74. The inner needle 28 is connected to and extends away from the non-rotating portion 74 of the cartridge 62 into the outer tube 24.

An assembly of a pusher handle 20' and a pusher shaft 26' are arranged to be held at a proximal end of the housing channel 70 such that the pusher shaft extends through one of the cartridge chambers 76 and through the inner needle 28 lumen when the cartridge 62 is in its proximal position. The pusher handle 20' and a pusher shaft 26' are removable from the cartridge chamber 76 to permit the movable portion 72 of the cartridge 62 to be repositioned to align a different chamber with the inner needle 28, as will be explained.

In one particular embodiment, multiple clips 30, each in their own cartridge chamber 76, are arranged around the perimeter of the revolving cylinder 72 portion of the cartridge 62, as shown in FIG. 15. The assembly of the pusher handle 20' and pusher shaft 26' at the proximal end of the cylinder 72 are first removed, as in FIG. 14C, and then each individual chamber 76 is also brought into alignment one at a time. The cylinder 72 revolves around the longitudinal axis of the system 60 which allows alignment of each chamber with the clip channel of the inner needle 28 for deployment. That done, the pusher handle 20' and pusher shaft 26' are inserted again to move each clip 30 into the clip channel of the inner needle 28. FIG. 14B shows proximal movement of the cartridge 62 such that the pusher shaft 26' ejects the clip 30 from the inner needle 28. The inner needle 28 and cartridge 62 move a distance A approximately equal to the length of each clip 30 in its straightened shape and the clips curl toward their relaxed shapes when ejected. The outer tube 24 remains in place, preferably with its stop flange staying in contact with the target tissue or material layer. The next clip 30 is then aligned via the rotation of the cylinder 72. The chambers may be internal or external to the cylinder 72. This embodiment allows multiple clips 30 to be deployed without the user reloading the system 60.

While particular forms of the invention have been illustrated and described, it will be apparent that various modifications can be made without departing from the spirit and scope of the invention. For example, in addition to the delivery device discussed herein, the clips of the present invention could also be delivered though a catheter or a laparoscopic type instrument. The delivery system could also be modified such that the clips could be delivered through a flexible catheter. The delivery device could also be placed on the end of a long shaft for delivery in a deep surgical incision such as an aortic valve replacement through a thoracotomy. Accordingly, it is not intended that the invention be limited, except as by the appended claims.

What is claimed is:

1. A method for securing a prosthetic heart valve to a native heart valve annulus, comprising the steps of:

inserting a prosthetic heart valve having a securing ring to a native heart valve annulus such that the securing ring is in contact with the annulus;

advancing a securing device toward the prosthetic heart valve, the securing device having an outer tube with a lumen and a stop flange on a distal end thereof, an inner needle having a sharpened end and sized and aligned to pass through the outer tube lumen and extend from the outer tube stop flange, self-cinching clips made of a super-elastic material held in a substantially straight constrained configuration within a lumen in the inner needle, a self-cinching clip having a non-linear relaxed configuration when unconstrained, and a pusher shaft sized to fit through the inner needle lumen and expel the clip therefrom, wherein the inner needle is mounted for movement along a channel in a housing, and the pusher shaft has a fixed position at a proximal end of the channel such that proximal movement of the inner needle causes the pusher shaft to expel the clip from the inner needle, and wherein the securing device has a cartridge with a plurality of chambers each sized to hold one of the self-cinching clips in its constrained configuration, the inner needle being attached to the cartridge and the entire cartridge being movable along the housing channel between a distal position and a proximal position;

puncturing the prosthetic heart valve securing ring and native heart valve annulus using the sharpened end of the inner needle until the stop flange contacts the securing ring and the inner needle projects beyond a distal side of the annulus;

partially expelling the clip from the inner needle using the pusher shaft so that a portion of the clip beyond the distal side of the annulus returns to its relaxed configuration;

withdrawing the inner needle to a proximal side of the securing ring;

fully expelling the clip from the inner needle so that a portion of the clip on the proximal side of the securing ring returns to its relaxed configuration, thus holding the securing ring against the annulus; and repeating the steps of puncturing, partially expelling, withdrawing and fully expelling to deploy multiple clips around the securing ring, including sequentially aligning different chambers with the pusher shaft and inner needle to sequentially deploy multiple clips.

2. The method of claim 1, wherein the native heart valve annulus is an aortic valve annulus, and the securing device is advanced along an aorta and the clips are deployed entirely from an outflow side of the valve.

3. The method of claim 1, wherein the self-cinching clip, in its relaxed configuration, has a spiral shape having two open ends terminating at different locations.

4. The method of claim 1, wherein the self-cinching clip, in its relaxed configuration, has a circular shape with two ends terminating at approximately the same location.

5. The method of claim 1, wherein the self-cinching clip, in its relaxed configuration, has a semicircle shape with two ends terminating at approximately the same location.

6. The method of claim 1, wherein the securing device has a cartridge with a plurality of chambers each sized to hold one of the self-cinching clips in its constrained configuration, and the method includes sequentially aligning different chambers with the inner needle to sequentially deploy multiple clips.

7. The method of claim 1, wherein the cartridge has a proximal portion rotatable about a central axis parallel to a proximal/distal direction and relative to a distal portion to which the inner needle attaches, the distal portion having a throughbore aligned with the inner needle lumen and aligned with sequential chambers when the proximal portion rotates, and wherein the pusher shaft is insertable and removable from the cartridge chambers to permit the proximal portion of the cartridge to rotate to align different cartridge chambers with the pusher shaft and throughbore and inner needle lumen, the method including sequentially rotating the proximal portion of the cartridge to align different chambers with the inner needle lumen and sequentially deploy multiple clips.

8. A method for securing a prosthetic heart valve to a native heart valve annulus, comprising the steps of:

inserting a prosthetic heart valve having a securing ring to a native heart valve annulus such that the securing ring is in contact with the annulus;

advancing a securing device toward the prosthetic heart valve, the securing device having an outer tube with a lumen and a stop flange on a distal end thereof, the outer tube also having an axial slot that extends to the stop flange, an inner needle having a sharpened end and sized and aligned to pass through the outer tube lumen and extend from the outer tube stop flange, the inner needle having a clip channel that extends to the sharpened end and being rotatable with respect to the outer tube, a self-cinching clip made of a super-elastic material held in a substantially straight constrained configuration within a lumen in the inner needle, the clip having a non-linear relaxed configuration when unconstrained, and a pusher shaft sized to fit through the inner needle lumen and expel the clip therefrom;

puncturing the prosthetic heart valve securing ring and native heart valve annulus using the sharpened end of the inner needle until the stop flange contacts the securing ring and the inner needle projects beyond a distal side of the annulus;

advancing the clip through the inner needle using the pusher shaft until the clip is located adjacent the clip channel in the inner needle and the axial slot in the outer tube;

rotating the outer tube to align the clip channel in the inner needle and the axial slot in the outer tube so that a portion of the clip beyond the distal side of the annulus returns to its relaxed configuration and a portion of the clip on the proximal side of the securing ring returns to its relaxed configuration, thus holding the securing ring against the annulus; and repeating the steps of puncturing, partially expelling, withdrawing and fully expelling to deploy multiple clips around the securing ring.

9. The method of claim 8, wherein the native heart valve annulus is an aortic valve annulus, and the securing device is advanced along an aorta and the clips are deployed entirely from an outflow side of the valve.

10. The method of claim 8, wherein the self-cinching clip, in its relaxed configuration, has a circular shape with two ends terminating at approximately the same location.

11. The method of claim 8, wherein the self-cinching clip, in its relaxed configuration, has a semicircle shape with two ends terminating at approximately the same location.

12. The method of claim 8, wherein the securing device has a cartridge with a plurality of chambers each sized to hold one of the self-cinching clips in its constrained configuration, and the method includes sequentially aligning different chambers with the inner needle to sequentially deploy multiple clips.

13. The method of claim 8, wherein the inner needle is mounted for movement along a channel in a housing, and the pusher shaft has a fixed position at a proximal end of the channel such that proximal movement of the inner needle causes the pusher shaft to advance the clip through the inner needle.

14. The method of claim 13, wherein the securing device has a cartridge with a plurality of chambers each sized to hold one of the self-cinching clips in its constrained configuration, the inner needle being attached to the cartridge and the entire cartridge being movable along the housing channel between a distal position and a proximal position, and the method includes sequentially aligning different chambers with the inner needle to sequentially deploy multiple clips.

15. The method of claim 14, wherein the cartridge has a proximal portion rotatable about a central axis parallel to a proximal/distal direction and relative to a distal portion to which the inner needle attaches, the distal portion having a throughbore aligned with the inner needle lumen and aligned with sequential chambers when the proximal portion rotates, and wherein the pusher shaft is insertable and removable from the cartridge chambers to permit the proximal portion of the cartridge to rotate to align different cartridge chambers with the pusher shaft and throughbore and inner needle lumen, the method including sequentially rotating the proximal portion of the cartridge to align different chambers with the inner needle lumen and sequentially deploy multiple clips.

* * * * *